United States Patent
Ahmadi Noorbakhsh

(10) Patent No.: US 11,565,061 B2
(45) Date of Patent: Jan. 31, 2023

(54) RESUSCITATION MANAGEMENT SYSTEM BASED ON RADIOFREQUENCY IDENTIFICATION FOR MANUAL RESUSCITATORS

(71) Applicant: Siavash Ahmadi Noorbakhsh, Tehran (IR)

(72) Inventor: Siavash Ahmadi Noorbakhsh, Tehran (IR)

( * ) Notice: Subject to any disclaimer, the term of this patent is extended or adjusted under 35 U.S.C. 154(b) by 111 days.

(21) Appl. No.: 17/207,654

(22) Filed: Mar. 20, 2021

(65) Prior Publication Data

US 2021/0209320 A1 Jul. 8, 2021

Related U.S. Application Data

(60) Provisional application No. 62/993,728, filed on Mar. 24, 2020.

(51) Int. Cl.
*A61M 16/00* (2006.01)
*G06K 7/10* (2006.01)
*G06K 19/077* (2006.01)

(52) U.S. Cl.
CPC .... *A61M 16/0084* (2014.02); *A61M 16/0078* (2013.01); *G06K 7/10366* (2013.01); *G06K 19/07758* (2013.01); *A61M 2205/0272* (2013.01); *A61M 2205/3317* (2013.01); *A61M 2205/3327* (2013.01); *A61M 2205/3334* (2013.01); *A61M 2205/502* (2013.01);
(Continued)

(58) Field of Classification Search
CPC .......... A61M 16/0084; A61M 16/0078; A61M 2205/0272; A61M 2205/3317; A61M 2205/3327; A61M 2205/3334; A61M 2205/502; A61M 2205/52; A61M 2205/581; A61M 2205/582; A61M 2205/583; A61M 2205/6054; A61M 2230/40; A61M 16/208; A61M 2205/10; A61M 2205/18; A61M 2205/505; A61M 2205/584; G06K 7/10366; G06K 19/07758; G16H 20/40; G16H 40/63
See application file for complete search history.

(56) References Cited

U.S. PATENT DOCUMENTS 10,532,174 B2 * 1/2020 Al-Ali ................ A61M 16/021
2013/0296747 A1 * 11/2013 Perreault ............. A61H 31/005
601/41

FOREIGN PATENT DOCUMENTS

EP 3300713 A1 * 4/2018 .......... A61H 31/005

* cited by examiner

*Primary Examiner* — Tuyen K Vo
(74) *Attorney, Agent, or Firm* — Bajwa IP Law Firm; Haris Zaheer Bajwa

(57) ABSTRACT

A resuscitation management system for a manual resuscitator may include a radio frequency identification (RFID) tag that may be configured to be mounted on a first side of a bag of the manual resuscitator. The RFID tag may be configured to transmit information indicative of the presence of the RFID tag. The system may further include an RFID reader that may be configured to be mounted on an opposite second side of the bag. The RFID reader may be configured to generate an output signal corresponding to the presence of the RFID tag responsive to receiving the information transmitted by the RFID tag. The RFID reader may be configured to receive the information transmitted by the RFID tag responsive to the RFID tag being at a distance from the RFID reader smaller than a predetermined threshold.

19 Claims, 9 Drawing Sheets

(52) U.S. Cl.
CPC ... *A61M 2205/52* (2013.01); *A61M 2205/581* (2013.01); *A61M 2205/582* (2013.01); *A61M 2205/583* (2013.01); *A61M 2205/6054* (2013.01); *A61M 2230/40* (2013.01)

RESUSCITATION MANAGEMENT SYSTEM BASED ON RADIOFREQUENCY IDENTIFICATION FOR MANUAL RESUSCITATORS

CROSS-REFERENCE TO RELATED APPLICATION

This application claims the benefit of priority from U.S. Provisional Patent Application Ser. No. 62/993,728, filed on Mar. 24, 2020, and entitled "MANAGEMENT DEVICE FOR BAG-VALVE-MASK RESUSCITATORS," which is incorporated herein by reference in its entirety.

TECHNICAL FIELD

The present disclosure generally relates to resuscitators, particularly relates to manual resuscitators. More particularly, the present disclosure relates to systems and methods for controlling breathing parameters of a manual resuscitator, such as breathing rate, tidal volume, minute ventilation, breathing pace, and inspiratory to expiratory ratio.

BACKGROUND

Respiratory failure generally presents itself in the form of respiratory insufficiency or complete respiratory arrest. Acute respiratory failure may lead to high morbidity and mortality rate if not treated early. The mortality rate for people with acute respiratory failure is between 25 to 83% among in-hospital patients and even higher for out of hospital patients. The morbidity caused by acute respiratory failure is mainly due to low blood oxygenation, which may lead to extensive and irreversible destruction to brain, heart, and other organs.

Acute respiratory failure usually responds very well to early intervention. Patients who are treated early using artificial breathing devices have a high rate of survival and a good prognosis. In this regard, a simple manual breathing device is usually readily available to begin artificial breathing in an emergency. Bag-Valve-Mask devices are one of the most efficient and readily available manual breathing devices. Although bag-valve-masks have saved lives of many patients, it has recently been revealed that improper use of bag-valve-masks may lead to a high rate of mortality and morbidity as discussed in further detail below.

According to the latest guidelines of the American Heart Association (AHA), the artificial breathing rate is an important parameter determining the survival of patients with respiratory or cardio-respiratory arrest. The AHA has determined the optimum target rate of artificial breathing for adults with respiratory arrest as 10-12 breaths per minute. In addition, the breathing rate should be 2-10 breaths per minute for adults with cardiorespiratory arrest. The breathing rate differs for infants, children, and people with underlying diseases.

However, several studies have shown significant non-compliance between guideline recommendations and real practice. This non-compliance not only happens by the general public, or inexperienced members of the medical team but also by experienced medical personnel. For example, in one study it was revealed that even highly experienced paramedics were consistently ventilating cardiac arrested patients with breathing rates significantly higher than guidelines (i.e., hyperventilating patients). No rescuer in that study ventilated patients according to the guidelines, and they usually tended to ventilate patients with rates triple times or more than the recommended rates which substantially decreases the survival rates of the patients or causes irreversible life-long brain injuries.

The mechanism of the detrimental effect of hyperventilation during a respiratory arrest is partly understood. Hyperventilation contributes to increased intrathoracic pressure and may eventually lead to decreased heart coronary vessels' perfusion pressure, decreased cerebral perfusion pressure, induction of respiratory alkalosis, decreased cardiac output, loss of cerebrovascular autoregulation, brain cell hypoxemia, and initial and/or rebound increases in intracranial pressure in traumatic brain injury patients. The major problem is that all these detrimental effects are being inadvertently caused by medical teams and are not related to the main disease of a patient.

Previous attempts for preventing hyperventilation problem in bag-valve-masks were based on "educational methods", "systems for controlling breathing rate", and "cardiopulmonary resuscitation (CPR) metronomes". Despite educational training sessions, literature still shows the tendency of even experienced rescuers toward inappropriate hyperventilation. Researchers believe that some reasons that may cause rescuers to ignore the guidelines and hyperventilate patients are the high levels of stress in the setting of an emergency visit of a (cardio)pulmonary arrested patient, complex processes of resuscitation that may cause human error in counting the breathing, and an impacted mental state of a rescuer encountering unstable vital signs of an arrested patient despite extensive resuscitation efforts.

Efforts to develop systems for controlling breathing rate has led to the development of electronic control devices having sets of sensors being placed in the airway of bag-valve-masks and providing information via different types of displays. These electronic systems may include various sensors; such as pressure sensors, flow-rate sensors, oxygen sensors, carbon dioxide sensors, alcohol sensors, and sensors for detecting probable drugs in a patients' exhalation. These control devices may measure various respiratory parameters such as airflow rate, breathing rate, breathing air pressure, and other relevant parameters.

Since sensors of the prior art control devices are placed in an airway of a bag-valve-mask resuscitator, they need to be sterilized before being used for each patient, otherwise they may transmit diseases between patients. The sterilization could be accomplished by either making whole control device or at least the sensors single-use. However, this may lead to a significant increase in the price of a control device. Since bag-valve-masks are being largely used in prehospital and in-hospital emergencies, even a slight increase in their price due to new technology may face rejection by health system managers.

On the other hand, the whole control device or at least sensors of a control device may be made reusable. However, due to the sensitive electronic structures of these control devices, they cannot be autoclaved using common pressurized high-temperature water steam autoclaves. In this regard, they require advanced sterilization methods such as gamma-ray, plasma, or ethylene oxide sterilization. These methods are expensive and require specialized equipment, not readily available in many healthcare facilities. Apart from the method of sterilization, the collection, and processing of a large number of these control devices for sterilization require specific logistics which adds a burden to the already complex logistics of healthcare facilities.

It should also be noted that in routine practice, during the transfer of patients by ambulances, bag-valve-masks are usually moved along with patients into hospitals. Since ambulance units in many regions are independent of hospitals, management of the reusable control devices utilized in bag-valve-masks would be challenging. In one scenario, a control device may be transferred along with a bag-valve-mask and a patient to a hospital. However, returning such a large number of control devices to ambulance services would be a complex and costly practice.

In another scenario, a control device may be detached from a bag-valve-mask during the handover of a patient from an ambulance to a hospital. However, the detachment of an intra-airway sensor would require major manipulation of a bag-valve-mask and consequent pause of the breathing of a (cardio)respiratory arrested patient. There also needs to be another device (compatible with the type of the bag-valve-mask being used) to be connected to the bag-valve-mask at the hospital. This practice may be considered as an unnecessary interruption of the resuscitation of a critically ill patient and may even have legal consequences.

Apart from the aforementioned sterilization issue, most of the prior art control devices may require a completely new design for a manual resuscitation device. In this context, introducing a completely new resuscitation device would be challenging from various points of view, such as acquiring medical permissions, proving their efficacy, introduction of a new device to the healthcare systems, changing users' minds to accept them as a new standard for resuscitation procedures, educating a large number of people on how to use the new resuscitation devices, and amending regulatory guidelines to consider these new resuscitation devices as accepted systems for breathing.

Furthermore, producing such new resuscitation devices require a significant change in current production lines of manufacturers and the future state of current millions of bag-valve-masks in markets and healthcare systems is unknown. Therefore, although using prior art systems might improve the quality of patients' resuscitation, the costs of introducing them to the medical community may not justify their benefits.

As mentioned before, a CPR metronome may be utilized to prevent hyperventilation problem. A CPR metronome is basically a ticking clock that produces audio or visual indications. For example, to deliver 20 breaths per minute, a CPR metronome may tick every 3 seconds. A user who is performing an intervention such as a cardiac massage or resuscitation utilizing a manual resuscitator is supposed to perform a single massage or resuscitation with each indication made by an exemplary CPR metronome. However, if a user fails to do so, a CPR metronome cannot compensate for a missed intervention. In real practice, a resuscitation process may be far more complex and there is no guarantee that a user can adjust themselves with a CPR metronome indication. For example, while a CPR metronome is ticking, in a first exemplary scenario, a user may be engaged with tasks other than giving respiration. In a second exemplary scenario, a user may be stressed out due to unstable vital signs of an arrested patient and may be desperately delivering excess numbers of respirations. In the first exemplary scenario, a CPR metronome may not compensate for a missed breathing, and in the second exemplary scenario a CPR metronome may not produce an alarm for a user to stop hyperventilating. Furthermore, a CPR metronome may not be capable of evaluate quality of given ventilations. In an exemplary scenario, a user may not adequately squeeze the bag due to being tired of performing CPR for a while. In this exemplary scenario, a CPR metronome may not detect an improperly delivered breathing.

There is, therefore, a need for a simple and cost-effective control device that may be utilized in a currently available bag-valve-mask resuscitator without being installed in an airway of such bag-valve-mask resuscitator. There is further a need for a device that may evaluate quality and quantity of resuscitation breathings, and provide real-time guidance to a user or a caregiver to achieve proper resuscitation parameters.

SUMMARY

This summary is intended to provide an overview of the subject matter of the present disclosure and is not intended to identify essential elements or key elements of the subject matter, nor is it intended to be used to determine the scope of the claimed implementations. The proper scope of the present disclosure may be ascertained from the claims set forth below in view of the detailed description and the drawings.

According to one or more exemplary embodiments, the present disclosure is directed to a resuscitating management system for a manual resuscitator. An exemplary resuscitating management system may include a radio frequency identification (RFID) tag that may be configured to be mounted on a first side of a bag of an exemplary manual resuscitator. An exemplary RFID tag may be configured to transmit information indicative of the presence of an exemplary RFID tag. An exemplary system may further include an RFID reader that may be configured to be mounted on an opposite second side of an exemplary bag. An exemplary RFID reader may be configured to generate an output signal corresponding to the presence of an exemplary RFID tag responsive to receiving the information transmitted by an exemplary RFID tag. An exemplary RFID reader may be configured to receive the information transmitted by an exemplary RFID tag responsive to an exemplary RFID tag being at a distance from an exemplary RFID reader equal or smaller than a predetermined threshold.

An exemplary bag may be squeezable between a decompressed state and a compressed state. An exemplary RFID tag and an exemplary RFID reader may be at a first distance from each other in an exemplary decompressed state. An exemplary RFID tag and an exemplary RFID reader may be at a second distance from each other in an exemplary compressed state. The predetermined threshold may be set equal to the second distance. The second distance may be less than the first distance.

In an exemplary embodiment, the information transmitted by the RFID tag may include at least a radio frequency signal. An exemplary RFID reader may further be configured to measure a strength of an exemplary radio frequency signal that may be transmitted by an exemplary RFID tag and to generate a signal strength data corresponding to an exemplary measured strength of an exemplary radio frequency signal.

In an exemplary embodiment, an exemplary system may further include a processing unit that may be coupled to an exemplary RFID reader. an exemplary processing unit may include at least one processor, and at least one memory that may be coupled to at least one exemplary processor. At least one exemplary memory may store executable instructions to urge at least one exemplary processor to receive a plurality of output signals from an exemplary RFID reader, associate each received output signal of plurality of exemplary output signals with a delivered ventilation and calculate a breathing rate by counting exemplary delivered ventilations during a time interval.

In an exemplary embodiment, at least one exemplary memory may further store executable instructions to urge at least one exemplary processor to receive a plurality of signal strength data from an exemplary RFID reader during an exemplary time interval, calculate a change in signal strength over an exemplary time interval based on plurality of exemplary signal strength data, associate an exemplary change in signal strength over an exemplary time interval with a compression/decompression speed of an exemplary bag, and calculate an inspiratory to expiratory (I:E) ratio based at least in part on an exemplary compression/decompression speed of an exemplary bag.

In an exemplary embodiment, at least one exemplary memory may further store executable instructions to urge at least one exemplary processor to calculate a distance between an exemplary RFID reader and an exemplary RFID tag at a given instance by correlating an exemplary signal strength data received from an exemplary RFID reader at an exemplary given instance to an exemplary distance between an exemplary RFID reader and an exemplary RFID tag at an exemplary given instance, calculate a compression extent of an exemplary bag at an exemplary given instance by correlating an exemplary distance between an exemplary RFID reader and an exemplary RFID tag at an exemplary given instance to an exemplary compression extent of an exemplary bag. and calculate a tidal volume for each delivered ventilation by correlating an exemplary compression extent of an exemplary bag to a volume of breathing gases pushed out of an exemplary bag.

In an exemplary embodiment, at least one exemplary memory may further store executable instructions to urge at least one exemplary processor to calculate a minute ventilation by calculating a sum of an exemplary calculated tidal volumes for an exemplary delivered ventilations in one minute.

BRIEF DESCRIPTION OF THE DRAWINGS

The novel features which are believed to be characteristic of the present disclosure, as to its structure, organization, use and method of operation, together with further objectives and advantages thereof, will be better understood from the following drawings in which a presently exemplary embodiment of the present disclosure will now be illustrated by way of example. It is expressly understood, however, that the drawings are for illustration and description only and are not intended as a definition of the limits of the present disclosure. Embodiments of the present disclosure will now be described by way of example in association with the accompanying drawings in which.

DETAILED DESCRIPTION

Figure 1A:
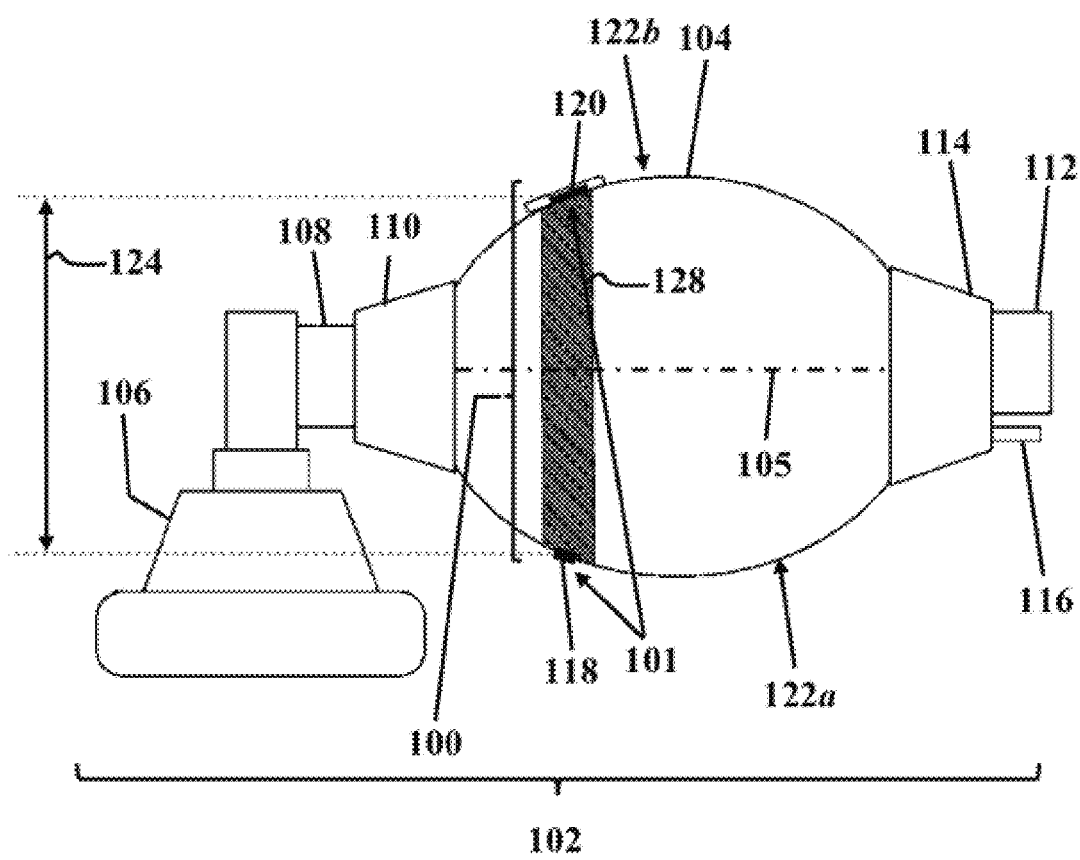
FIG. 1A illustrates a schematic side-view of a resuscitation management device mounted on a manual resuscitator, consistent with one or more exemplary embodiments of the present disclosure.

The novel features which are believed to be characteristic of the present disclosure, as to its structure, organization, use and method of operation, together with further objectives and advantages thereof, will be better understood from the following discussion.

The present disclosure is directed to exemplary embodiments of a system and method for resuscitation management that may be used for a manual resuscitator. An exemplary resuscitation management system may detect compression of a bag of a manual resuscitator and may associate each detected compression of the bag with a single breath delivered to a patient. An exemplary resuscitation management system may further generate an indication signal so as to provide information related to breathing rate of a patient to a user. Such information may guide a user to achieve a target breathing rate, which may determine the survival chance of a patient and may prevent damages related to improper ventilation of a patient, such as brain damages. A user may be a rescuer or a caregiver who is utilizing a manual resuscitator to help a patient breathe. As used herein, air, gas, and breathing gases may be used interchangeably and may refer to gaseous materials that a person may inhale or exhale for the purpose of respiration and may either include a single chemical element or a combination of various chemical elements.

An exemplary resuscitation management system may include a sensor assembly that may be configured to detect a state of a resuscitation bag between a compressed state and a decompressed state. An exemplary sensor assembly may include a sensing element and a sensible element, where sensing element may detect the presence of the sensible element in a certain read range. An exemplary read range may be adjusted to correspond to a compressed state of a resuscitation bag, which may allow for an exemplary sensing element to generate an output signal whenever an exemplary resuscitation bag is in a compressed state. In an exemplary embodiment, detecting the presence of an exemplary sensible element in a certain read range may further allow for detecting an inadequate compression of an exemplary resuscitation bag, since for an inadequate compression of an exemplary resuscitation bag, a distance between an exemplary sensing element and an exemplary sensible element is more than an exemplary read range. Consequently, such inadequate compression may not be associated with a breath delivered to a patient.

An exemplary sensing element and an exemplary sensible element may be mounted on an outer surface of an exemplary resuscitation bag without any contact with contents of the bag. Such isolation of breathing gases from an exemplary sensor assembly may eliminate risks of improper sterilization of a sensor assembly. In practice, no contamination may enter a flow of breathing gas from an exemplary sensing assembly since there is no contact between the breathing gases and an exemplary sensor assembly. Furthermore, an exemplary sensor assembly mounted on an outer surface of a resuscitating bag may allow for an easy and quick removal or change of an exemplary sensor assembly, which may be beneficial from a practical standpoint. For example, an exemplary resuscitation management device may be worn around an outer surface of an exemplary resuscitation bag by utilizing a flexible band. Such utilization of an exemplary flexible band to mount an exemplary resuscitation management device on an exemplary resuscitation bag may allow for easily and quickly mounting an exemplary resuscitation management device on resuscitation bags of various sizes. Furthermore, such flexible band mount may allow for easily and quickly removing an exemplary resuscitation management device by simply taking off an exemplary flexible band from around an exemplary resuscitation bag. In an exemplary scenario, such easy and quick removal of an exemplary resuscitation management device may be beneficial when an ambulance crew are handing over a (cardio)respiratory arrested patient to a hospital crew and need to quickly unmount their exemplary resuscitation management device from an exemplary resuscitation bag.

Figure 1B:
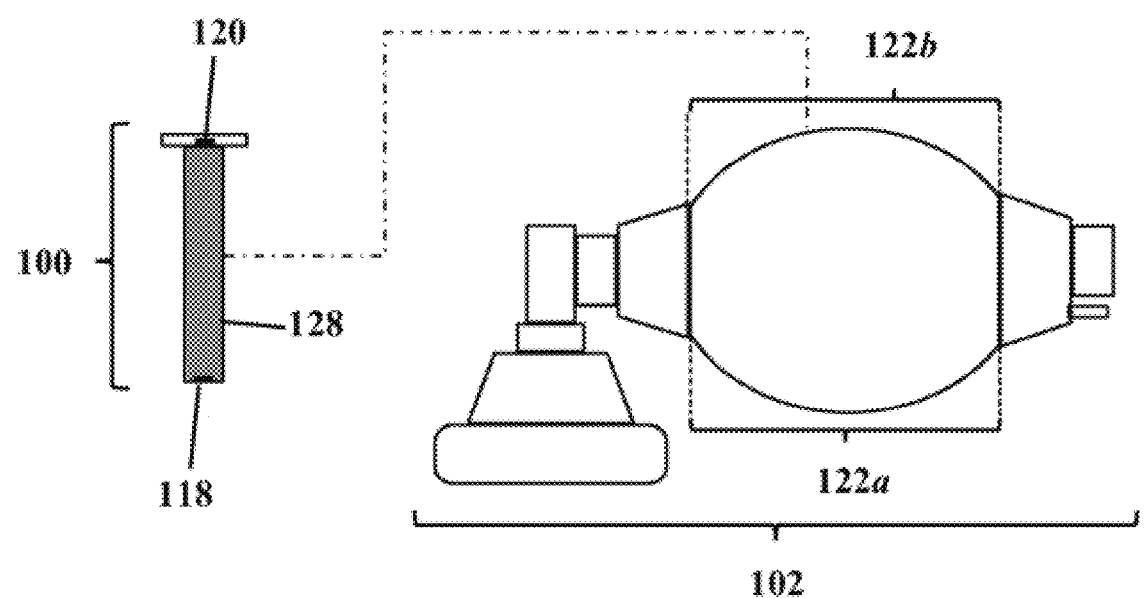
FIG. 1B illustrates a schematic exploded side-view of a resuscitation management device mounted on a manual resuscitator, consistent with one or more exemplary embodiments of the present disclosure.

FIG. 1A illustrates a schematic side-view of a resuscitation management device 100 mounted on a manual resuscitator 102, consistent with one or more exemplary embodiments of the present disclosure. FIG. 1B illustrates a schematic exploded side-view of resuscitation management device 100 mounted on manual resuscitator 102, consistent with one or more exemplary embodiments of the present disclosure. In an exemplary embodiment, manual resuscitator 102 may include a bag-valve-mask resuscitator, which may include a bag 104 that may be connected to a mask 106 via an anterior flow channel 108. In an exemplary embodiment, mask 106 may be placed on the nose and/or mouth of a patient (not illustrated) and may provide a sealed connection between a patient's airway and bag 104. In an exemplary embodiment, air or other breathing gases, such as oxygen may be manually pumped into a patient's airway by manually compressing and decompressing bag 104, which may be an inflatable or a self-inflatable bag. In an exemplary embodiment, manual resuscitator 102 may further include an anterior valve assembly 110 connected between bag 104 and mask 106 on anterior flow channel 108. In an exemplary embodiment, anterior valve assembly 110 may include a diaphragmatic or a shutter valve that may allow air or other breathing gases to pass through anterior flow channel 108 from bag 104 to mask 106 and may further divert exhaled breath of a patient to the atmosphere.

In an exemplary embodiment, bag 104 may receive air or other breathing gases from a posterior flow channel 112 that may be connected to bag 104 via a posterior valve assembly 114. In an exemplary embodiment, posterior valve assembly 114 may include a diaphragmatic or a shutter valve that may be a one-way valve allowing air or other breathing gases into bag 104. In an exemplary embodiment, a reservoir bag (not illustrated) may further be connected to posterior flow channel 112 and may provide a large volume of air or other breathing gases to bag 104 via posterior valve assembly 114. As mentioned before, in an exemplary embodiment, a user, such as a rescuer or a caregiver may squeeze bag 104 to deliver air or other breathing gases to a patient via mask 106. When bag 104 is released by a user, bag 104 may be decompressed or self-inflated and fresh air or other breathing gases may refill bag 104 either through posterior flow channel 112 or other inlet tubes, such as inlet tube 116.

In an exemplary embodiment, manual resuscitator 102 may include any other type of patient airway interface other than mask 106, for example, an endotracheal tube or a laryngeal mask may further be used instead of mask 106. As used herein, a patient airway interface may refer to any kind of device that may connect manual resuscitator 102 to a patient's airway.

In an exemplary embodiment, each time bag 104 is squeezed by a user, one positive pressure flow of a breathing gas may be provided to a patient and may be counted as a single respiration or breath. In an exemplary embodiment, manual resuscitator 102 may be of different sizes to fit different age groups, such as infants, children, and adults. For each age group, a proper range of breathing rate, inspiratory time to expiratory time (I:E) ratio, tidal volume, and minute ventilation should be provided to a patient, where such proper breathing rate, I:E ratio, tidal volume, or minute ventilation, are referred to herein as a target breathing rate, a target I:E ratio, a target tidal volume, or a target minute ventilation, respectively. As used herein, a breathing rate range may refer to a number of respirations or breaths provided by manual resuscitator 102 per minute or other reference time periods. For example, 10 to 12 respirations per minute in an adult and 12 to 20 respirations per minute in a child may be considered as a target respiratory or breathing rate range.

In an exemplary embodiment, a target range of I:E ratio may refer to the ratio between an inspiratory time and an expiratory time. For example, I:E ratio of 1:2 to 1:3 in an adult, or I:E ratio of 1:1.5 to 1:2 in an infant may be considered as a target I:E ratio. In an exemplary embodiment, a target range of tidal volume may refer to a volume of air delivered to lungs of a patient with each breath by an exemplary manual resuscitator. For example, a tidal volume of 500 to 600 ml in an adult, or a tidal volume of 100 to 200 ml in a child may be considered as a target tidal volume. In an exemplary embodiment, a target minute ventilation may refer to a volume of gas inhaled or exhaled from a person's lungs per minute or a volume of air delivered to lungs of a patient with each breath by an exemplary manual resuscitator. For example, a minute ventilation of 5 to 8 liter in an adult, or a minute ventilation of 240 to 360 mL/kg in an infant may be considered as a target minute ventilation.

In an exemplary embodiment, resuscitation management device 100 that may be mounted on bag 104 of manual resuscitator 102, may be configured to manage at least one of a respiration or breathing rate, an I:E ratio, a tidal volume, or a minute ventilation that may be provided by a user to a patient by utilizing manual resuscitator 102. In other words, resuscitation management device 100 may help a user to deliver at least one of a target respiratory or breathing rate, a target I:E ratio, a target tidal volume, or a target minute ventilation to a patient, based at least in part on age group and medical condition of that patient. To this end, in an exemplary embodiment, resuscitation management device 100 may be configured to calculate at least one of a respiration rate or breathing rate, or an I:E ratio by counting the number of times bag 104 is squeezed by a user, and calculate at least one of a tidal volume, or a minute ventilation by measuring the extent of squeezing of bag 104 by a user, and then based at least in part on one of the calculated breathing rate, the calculated I:E ratio, the calculated tidal volume, or the calculated minute ventilation may provide a user with audio, visual, tactile, or mechanical guidelines as to how to proceed with the resuscitation process.

In an exemplary embodiment, resuscitation management device 100 may include a sensor assembly 101 that may be mounted on bag 104 of manual resuscitator 102. In an exemplary embodiment, sensor assembly 101 may include a sensible element 118 that may be mounted on a first side 122a of bag 104. In an exemplary embodiment, sensible element 118 may be configured to transmit information that may be indicative of the presence of sensible element 118. For example, such information transmitted by sensible element 118 may include a radio frequency signal. In an exemplary embodiment, sensor assembly 101 may further include a sensing element 120 that may be mounted on an opposite second side 122b of bag 104. In an exemplary embodiment, sensing element 120 may be configured to generate an output signal corresponding to the presence of sensible element 118 responsive to receiving the information transmitted by sensible element 118. To this end, in an exemplary embodiment, sensing element 120 may be configured to receive the information transmitted by sensible element 118 responsive to sensible element 118 being at a distance from sensing element 120 equal to or smaller than a predetermined threshold. In other words, sensing element 120 may sense the presence of sensible element 118 when a distance 124 between sensible element 118 and sensing element 120 may be equal to or less than a predetermined threshold.

In an exemplary embodiment, sensing element 120 may be configured to measure a signal strength of a radio frequency signal emitted by sensible element 118 and to associate the measure signal strength with distance 124 between sensible element 118 and sensing element 120. In an exemplary embodiment, sensing element 120 may be configured to generate an output signal responsive to distance 124 between sensible element 118 and sensing element 120 being equal to or less than a predetermined threshold.

In an exemplary embodiment, sensing element 120 and sensible element 118 may be mounted anywhere along a longitudinal axis 105 of bag 104, such that sensing element 120 and sensible element 118 may be aligned with each other along an axis perpendicular to longitudinal axis 105. When bag 104 is compressed by a user, distance 124 between sensing element 120 and sensible element 118 decreases to a point where bag 104 is compressed adequately such that an adequate volume of breathing gases which is required for a proper breathing has been pushed out of bag 104 into a patient's airway via mask 106. In an exemplary embodiment, the predetermined threshold for distance 124 may be determined based on a calibration curve obtained for different sizes of bag 104. For example, for an adult bag, distance 124 may be at most approximately 13 cm and the predetermined threshold may be approximately 5 cm. For a child bag, distance 124 may be at most approximately 9 cm and the predetermined threshold may be approximately 3 cm. For an infant bag, distance 124 may be at most approximately 8 cm and the predetermined threshold may be approximately 3 cm.

Figure 2:
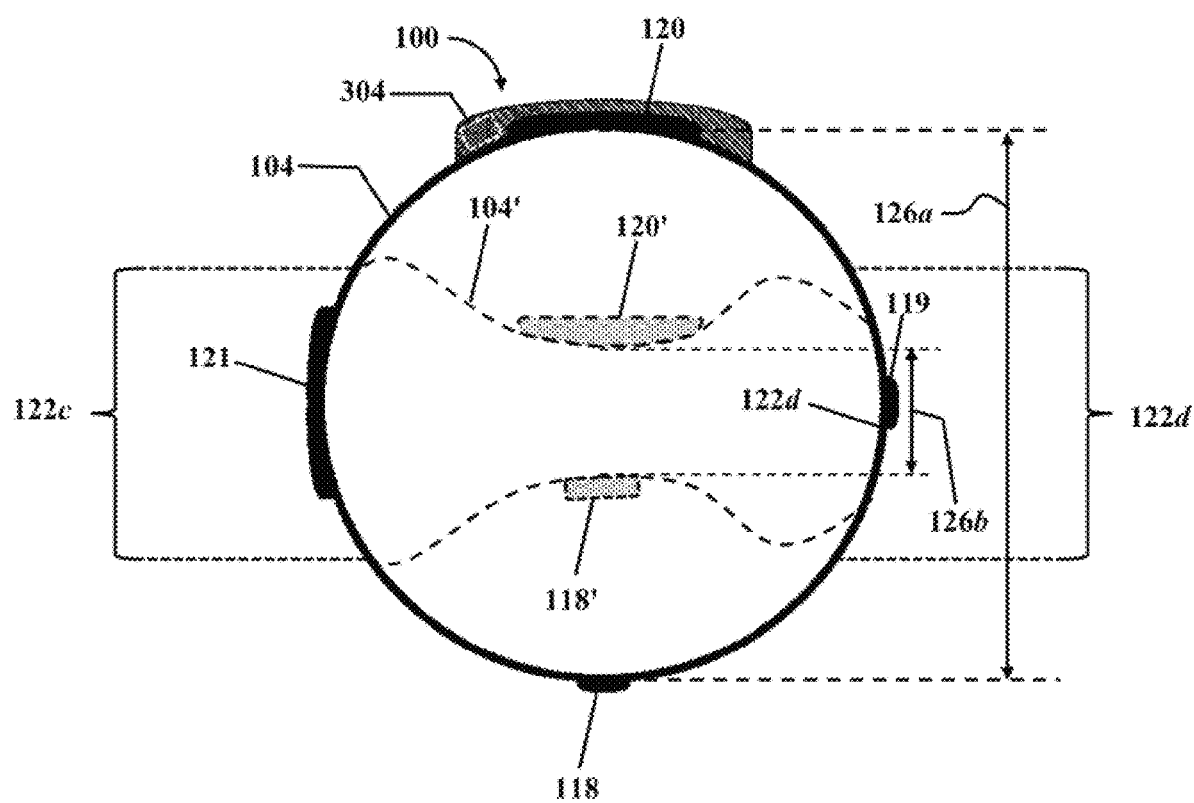
FIG. 2 illustrates a schematic front view of a resuscitation management device mounted on a manual resuscitator, consistent with one or more exemplary embodiments of the present disclosure.

FIG. 2 illustrates a schematic front view of resuscitation management device 100 mounted on manual resuscitator 102, consistent with one or more exemplary embodiments of the present disclosure. In an exemplary embodiment, bag 104 may be squeezable between a decompressed state (labeled by reference numeral 104) and a compressed state (illustrated by a dashed line labeled by reference numeral 104'). In an exemplary embodiment, sensible element 118 and sensing element 120 may be at a first distance 126a from each other in the decompressed state, while sensible element 118 and sensing element 120 may be at a second distance 126b from each other in the compressed state. For example, sensing element 120 is referred to by reference numeral 120' and sensible element 118 is referred to by reference numeral 118' in the compressed state illustrated in FIG. 2. In an exemplary embodiment, the predetermined threshold may be set equal to second distance 126b, where bag 104 is compressed adequately so that an adequate volume of breathing gases which is required for a proper breathing has been pushed out of bag 104. In an exemplary embodiment, an adequate amount of breathing gas may generally correspond to an entire inner volume of bag 104. As used herein, an entire volume may refer to 90±10% of an inner volume of bag 104.

In an exemplary embodiment, resuscitation management device 100 may include more than one sensor assembly that may be mounted on an outer surface of bag 104 of manual resuscitator 102. For example, resuscitation management device 100 may include a second sensor assembly that may include a second sensing element 121 that may be mounted on a third side 122c of bag 104 and a second sensible element 119 that may be mounted on a fourth side 122d of bag 104. In an exemplary embodiment, sensing element 121 and sensible element 119 may each be functionally and structurally similar to sensing element 120 and sensible element 118, respectively. In an exemplary embodiment, such configuration of more than one sensor assemblies mounted on an outer surface of bag 104 may allow for sensing deformation or compression of bag 104 along different directions.

In an exemplary embodiment, sensible element 118 may be configured to transmit the information via radio frequency signals. In an exemplary embodiment, sensible element 118 may include a radio frequency identification (RFID) tag that may be mounted on first side 122a of bag 104. In an exemplary embodiment, sensing element 120 may include an RFID reader that may be mounted on opposite second side 122b of bag 104. In other words, the RFID tag as sensible element 118 and the RFID reader as sensing element 120 may be aligned at opposite sides of bag 104 along an axis perpendicular to longitudinal axis 105 of bag 104.

In an exemplary embodiment, the RFID reader may be configured to generate and emit a radio signal with a certain strength within a read range. In an exemplary embodiment, an RIFD tag as sensible element 118 may further be configured to transmit the information responsive to receiving the radio signal emitted by the RFID reader. In an exemplary embodiment, the transmitted information by the RFID tag may include a first code made of a plurality of characters which is transmitted as a radio frequency signal. In an exemplary embodiment, an exemplary first code transmitted by an exemplary RFID tag may be unique to that exemplary RFID tag and may function as an identification code. In an exemplary embodiment, the read range of the RFID reader may be set equal to or less than the predetermined threshold so that the RFID reader may only read the information transmitted by the RFID tag when a distance between the RFID reader and the RFID tag is equal to or less than the predetermined threshold.

In an exemplary embodiment, an RFID tag may either be passive or active. An exemplary passive RFID tag may transmit information only when it is in the read range of an antenna of an exemplary RFID reader, as was described in the preceding paragraph. However, an exemplary active RFID may emit a radio frequency signal independently and without the need for receiving radio signals from an exemplary RFID reader. In an exemplary embodiment, sensible element 118 may include an active RFID tag that may be configured to generate and emit a radio signal with a certain level of strength that an RFID reader within a predetermined read range may only detect this level of strength of the radiofrequency signal. In other words, the active RFID tag may be configured to emit a radio frequency signal with a strength adjusted such that the radio frequency signal may be picked up by the RFID reader at a read range equal to or less than the predetermined threshold.

In an exemplary embodiment, sensible element 118 may include an active RFID tag that may be configured to generate and emit a radio signal with a certain level of strength that an RFID reader within a read range equal to or less than the first distance 126a between sensible element 118 and sensing element 120, may detect this radiofrequency signal. In other words, the active RFID tag may be configured to emit a radio frequency signal with a strength adjusted such that the radio frequency signal may be picked up by the RFID reader at a read range equal to or less than the first distance 126a between sensible element 118 and sensing element 120. In an exemplary embodiment, the radio signal transmitted by an exemplary active RFID tag may include information regarding the identity of the exemplary RFID tag and a signal strength. In an exemplary embodiment, the information transmitted by an exemplary active RIFD tag may include a first code that may be unique to that active RFID tag. In an exemplary embodiment, an RFID reader may be configured to associate the received signal strength with a distance between the RFID reader and the RFID tag. In an exemplary embodiment, the RFID reader may be configured to generate an output signal responsive to the distance between the RFID reader and the RFID tag being equal to or less than the predetermined ratio.

In an exemplary embodiment, sensing element 120 may further be configured to measure a strength of the radio frequency signal emitted by sensible element 118, to associate the measured strength of the radio frequency signal with a distance between sensing element 120 and sensible element 118, and to generate an output signal when the distance between sensing element 120 and sensible element 118 is equal to or less than the predetermined threshold.

In an exemplary embodiment, resuscitation management device 100 may further include a flexible band 128, on which sensing element 120 and sensible element 118 may be attached. In an exemplary embodiment, sensible element 118 may be attached on flexible band 128 spaced from sensing element 120 along a length of flexible band 128. In an exemplary embodiment, flexible band 128 may be wearable around bag 104, such that sensible element 118 may be positioned at first side 122a of bag 104 and sensing element 120 may be positioned at opposing second side 122b of bag 104 responsive to flexible band 128 being worn around bag 104. In an exemplary embodiment, flexible band 128 may be a rubber band that may be tightened around bag 104, such that no slipping motion may exist between sensing element 120, sensible element 118 and bag 104.

In an exemplary embodiment, other attachment mechanisms may as well be utilized for mounting sensing element 120 and sensible element 118 on bag 104. For example, sensing element 120 and sensible element 118, each may include a button or hook (not illustrated) that may be attached or fastened to another corresponding button or hook (not illustrated) on bag 104. In an exemplary embodiment, any other similar fastening solutions that may allow for mounting sensing element 120 and sensible element 118 on bag 104 without any unwanted translational or rotational movement of sensing element 120 and sensible element 118 with respect to an outer surface of bag 104, may also be utilized. In an exemplary embodiment, utilizing flexible band 128 may allow for mounting sensing element 120 and sensible element 118 on bag 104 without any changes made to bag 104. In other words, utilizing flexible band 128 may allow for mounting sensing element 120 and sensible element 118 on any resuscitation bag available to users.

Figure 3:
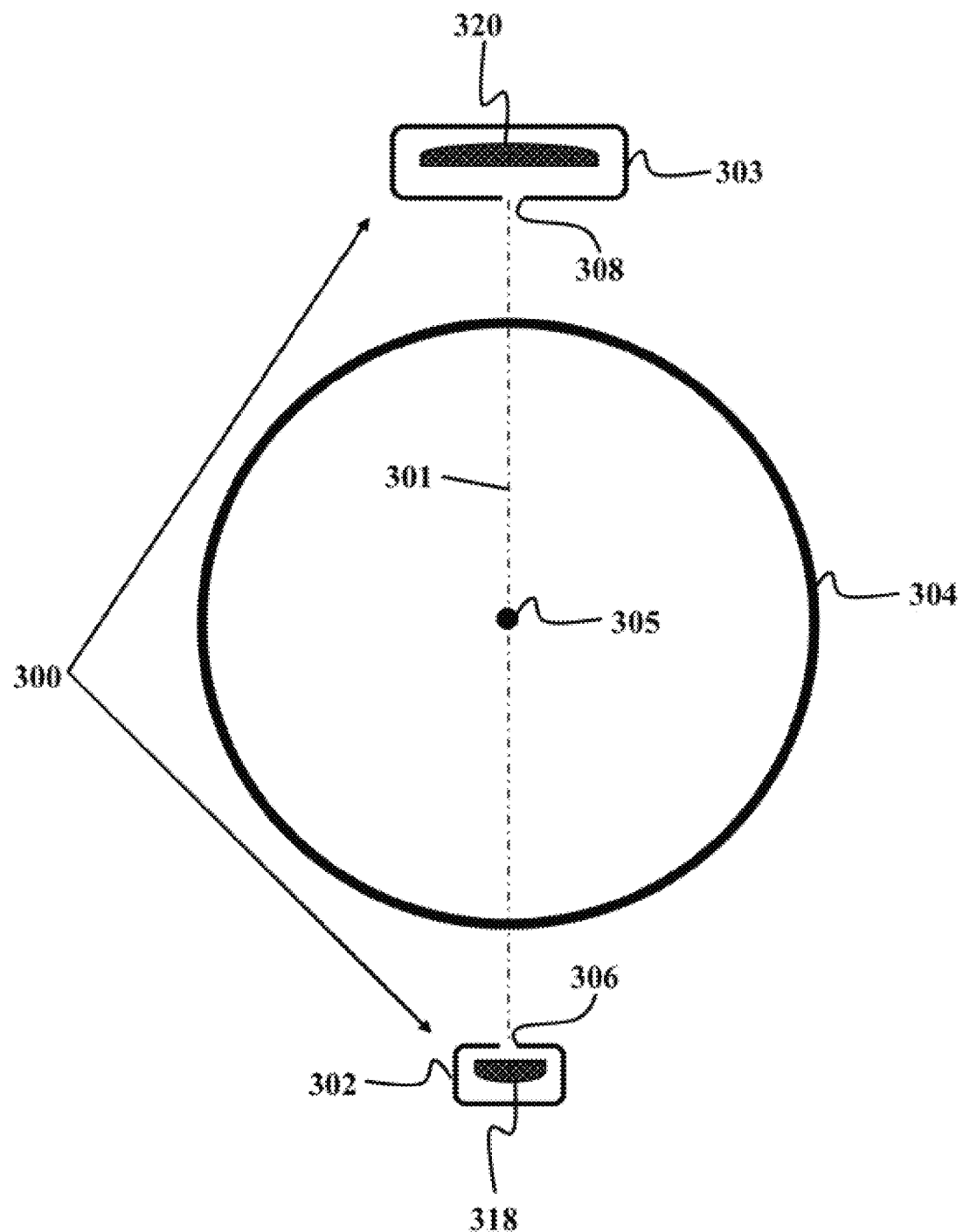
FIG. 3 illustrates a schematic front view of a resuscitation management device mounted on a manual resuscitator bag, consistent with one or more exemplary embodiments of the present disclosure.

FIG. 3 illustrates a schematic front view of a resuscitation management device 300 mounted on a manual resuscitator bag 304, consistent with one or more exemplary embodiments of the present disclosure. In an exemplary embodiment, resuscitation management device 300 may be similar to resuscitation management device 100 and may include a sensible element 318 similar to sensible element 118 and a sensing element 320 similar to sensing element 120. In an exemplary embodiment, sensible element 318 may include an RFID tag and sensing element 320 may include an RIFD reader.

In an exemplary embodiment, manual resuscitator bag 304 may be similar to bag 104 and may have a longitudinal axis 305 similar to longitudinal axis 105 of bag 104. In an exemplary embodiment, sensible element 318 and sensing element 320 may be mounted on opposite sides of manual resuscitator bag 304 along an axis 301. In an exemplary embodiment, axis 301 may be perpendicular to longitudinal axis 305. Referring to FIG. 3, longitudinal axis 305 is perpendicular to the view.

In an exemplary embodiment, the noise effect of ambient radio frequency emissions on an RFID tag as sensible element 318 and an RFID reader as sensing element 320 may be reduced or cancelled utilizing a first radiofrequency shield 302 that may enclose sensible element 318 and a second radiofrequency shield 303 that may enclose sensing element 320. In an exemplary embodiment, first radiofrequency shield 302 may include an enclosure that may encompass sensible element 318. In an exemplary embodiment, first radiofrequency shield 302 may further include a first window 306 that may be located at a side where sensible element 318 faces sensing element 320. In an exemplary embodiment, second radiofrequency shield 303 may include an enclosure that may encompass sensing element 320. In an exemplary embodiment, second radiofrequency shield 303 may further include a second window 308 that may be located at a side where sensing element 320 faces sensible element 318.

In an exemplary embodiment, first radiofrequency shield 302 and second radiofrequency shield 303 may be both made of galvanized steel or copper. In an exemplary embodiment, first radiofrequency shield 302 and second radiofrequency shield 303 may each be structured as a Faraday cage that may include a mesh of a conductive material.

Figure 4:
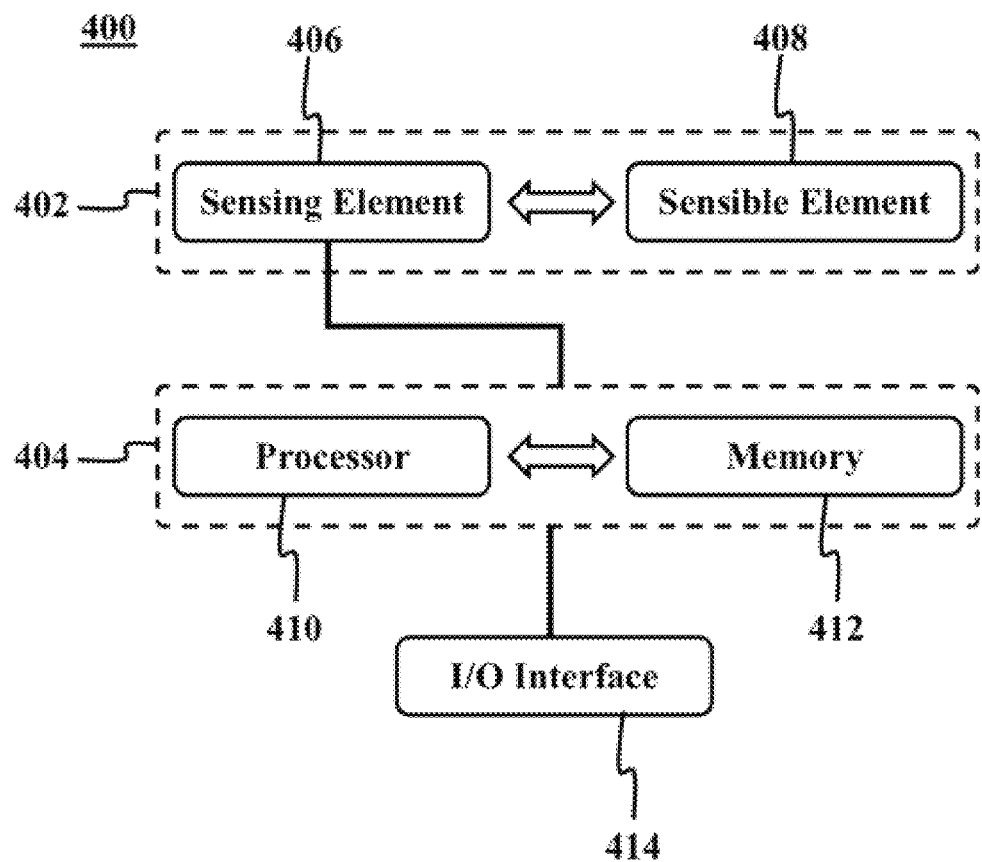
FIG. 4 illustrates a functional block diagram of a resuscitation management system, consistent with one or more exemplary embodiments of the present disclosure.

FIG. 4 illustrates a functional block diagram of a resuscitation management system 400, consistent with one or more exemplary embodiments of the present disclosure. In an exemplary embodiment, resuscitation management system 400 may be similar to resuscitation management device 100 and may include a sensor assembly 402, a processing unit 404 that may be coupled to sensor assembly 402. In an exemplary embodiment, sensor assembly 402 may include a sensing element 406 similar to sensing element 120, and a sensible element 408 similar to sensible element 118. In an exemplary embodiment, processing unit 404 may include a processor 410 and a memory 412 that may be coupled to processor 410. In an exemplary embodiment, memory 412 may store executable instructions to urge processor 410 to receive a plurality of output signals from sensing element 406, associate each received output signal of the plurality of output signals with a breathing and calculate a breathing rate by counting breaths during a time interval. For example, memory 412 may store executable instructions to urge processor 410 to associate the number of times an RFID tag as sensible element 118 is read by an RFID reader as sensing element 120 within a certain time interval with breathing rate.

As mentioned before, sensible element 408 may include an RFID tag that may transmit information indicative of the presence of the RFID tag. In an exemplary embodiment, the transmitted information may include a first code unique to the RFID tag and the RFID reader as sensing element 406 may be configured to generate an output signal responsive to reading the transmitted information sent by the RFID tag. In an exemplary embodiment, the output signal may also include the first code.

In an exemplary embodiment, memory 412 may store a second code and executable instructions to urge processor 410 to receive an output signal from sensing element 406, where the output signal includes the first code, determine if the first code and the second code are similar by comparing the first code and the second code, and associate the received output signal with a single appropriately delivered ventilation responsive to the first code and the second code being similar. In an exemplary embodiment, processor 410 may be configured to perform the abovementioned steps for a plurality of output signals received from sensing element 406 during a predetermined amount of time and calculate a breathing rate by counting the number of appropriately delivered ventilations during the predetermined amount of time.

In an exemplary embodiment, such utilization of an exemplary first code for identification of an exemplary RFID tag may allow for ensuring that only the output signals generated by sensing element 406 that contain the first code are considered by processor 410 to be indicative of an appropriately delivered ventilation. In other words, utilization of an exemplary first code for identification of an exemplary RFID tag may allow for ensuring that only the information indicative of the presence of sensible element 408 are considered by resuscitation management system 400. For example, if an irrelevant RFID tag (not illustrated) other than sensible element 408 may be present within the read range of sensing element 406, an output signals from sensing element 406 relating to that irrelevant RIFD tag may lack the information of the first code and thus processor 410 may not be urged to associate an output signal relating to that irrelevant RIFD tag with an appropriately delivered ventilation. Consequently, processor 410 may only associate a received output signal that is generated by sensing element 406 with a single successful breath, and the presence of other irrelevant RFID tags within the read range of sensing element 406 may not interfere with the proper functioning of resuscitation management system 400.

In an exemplary embodiment, sensing element 406 may be configured to measure a strength of a radio frequency signal emitted by sensible element 408 and associate the measured strength of the radio frequency signal with distance 124 between sensing element 120 and sensible element 118. To this end, a calibration curve or a lookup table may be obtained that may relate a strength of a radio frequency emitted by sensible element 408 to distance 124 between sensing element 120 and sensible element 118. In an exemplary embodiment, sensing element 406 may be configured to measure a strength of a radio frequency signal emitted by sensible element 408 and then utilize the obtained calibration curve or the lookup table to associate the measured strength of the radio frequency signal with distance 124 between sensing element 120 and sensible element 118.

In an exemplary embodiment, memory 412 may further store executable instructions to urge processor 410 to calculate the speed of compression or decompression of bag 104 based at least in part on a rate of change of distance 124 between sensing element 120 and sensible element 118 within a certain time interval. In an exemplary embodiment, memory 412 may further store executable instructions to urge processor 410 to use the calculated speed of compression or decompression of bag 104 to calculate at least one of an I:E ratio, and a breathing pace.

In an exemplary embodiment, resuscitation management system 400 may further include an input/output (I/O) interface 414 that may further be coupled to processing unit 404. In an exemplary embodiment, memory 412 may further store executable instructions to urge processor 410 to provide information on I/O interface 414 based at least in part on at least one of the calculated breathing rate, the calculated I:E ratio, the calculated tidal volume, and the calculated minute ventilation. In an exemplary embodiment, I/O interface 414 may include a display, where the information provided on the display may include one or a combination of numbers representing the calculated breath rate and target breathing rate. In an exemplary embodiment, the information provided on the display may further include the calculated I:E ratio and the target I:E ratio, the calculated tidal volume and the target tidal volume, or the calculated minute ventilation and the target minute ventilation, alarm notifications, and a timeline showing the past, and upcoming breathing timepoints according to the calculated breathing rate.

In an exemplary embodiment, the I/O interface may include an alarm that may be configured to produce a plurality of one or more audio, visual, tactile, or mechanical indications. In an exemplary embodiment, memory 412 may further store a target breathing rate range and executable instructions to urge processor 410 to compare the calculated breathing rate and the target breathing rate range, urge the alarm to produce at least one of a first audio indication, a first visual indication, a first tactile indication, and a first mechanical indication responsive to the calculated breathing rate being in the target breathing rate range, and urge the alarm to produce at least one of a second audio indication, a second visual indication, a second tactile indication, and a second mechanical indication responsive to the calculated breathing rate being outside the target breathing rate range.

In an exemplary embodiment, memory 412 may further store a plurality of target breathing rate ranges, where each breathing rate range of the plurality of target breathing rate ranges may be associated with an age group. I/O interface 414 may further be configured to receive data from a user, where the data may include at least one of a user-defined target breathing rate, age group, medical condition of patient, and a patient type (human or animal). In an exemplary embodiment, memory 412 may further store executable instructions to urge processor 410 to select a target breathing rate range based on the received data from the user, compare the calculated breathing rate and the selected target breathing rate range, urge the alarm to produce at least one of a first audio indication, a first visual indication, a first tactile indication, and a first mechanical indication responsive to the calculated breathing rate being in the selected target breathing rate range, and urge the alarm to produce at least one of a second audio indication, a second visual indication, a second tactile indication, and a second mechanical indication responsive to the calculated breathing rate being outside the selected target breathing rate range.

In an exemplary embodiment, memory 412 may further store a target I:E ratio, a target tidal volume or a target minute ventilation associated with various patient types (human or animal), age groups, and medical conditions. In an exemplary embodiment, memory 412 may further store executable instructions to urge processor 410 to select at least one of a target I:E ratio, a target tidal volume, and a target minute ventilation based at least in part on at least one of the received age group, the patient type, and the medical condition of a patient, calculate at least one of an I:E ratio, a tidal volume, a minute ventilation based on the received output signals from sensor assembly 402, compare at least one of the calculated I:E ratio, the calculated tidal volume, the calculated minute ventilation with the selected target values of I:E ratio, tidal volume, minute ventilation, and urge the alarm to produce at least one of an audio indication, a visual indication, a tactile indication, and a mechanical indication responsive to the calculated values being within selected target range or not.

Figure 5:
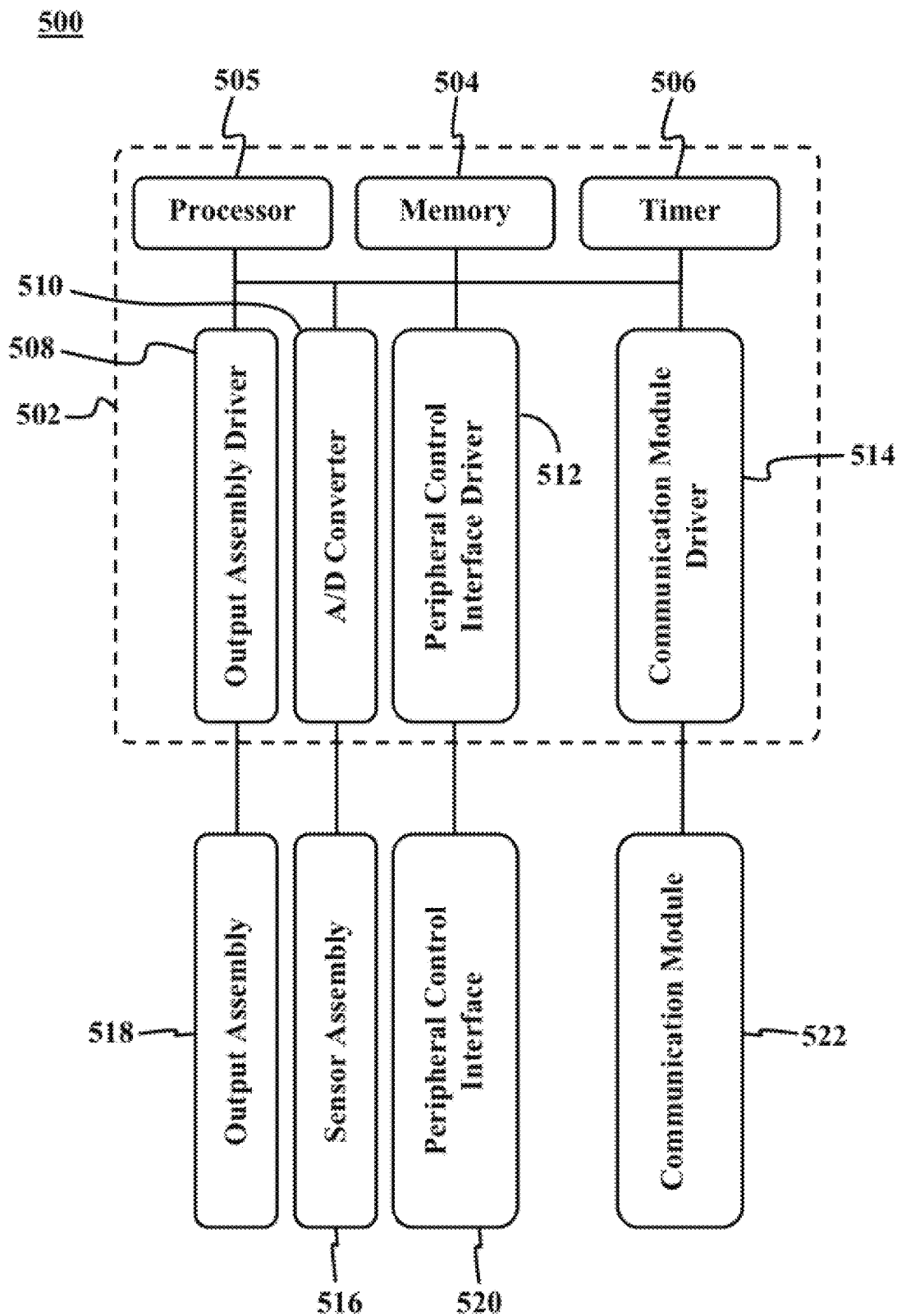
FIG. 5 illustrates a functional block diagram of a resuscitation management system, consistent with one or more exemplary embodiments of the present disclosure.

FIG. 5 illustrates a functional block diagram of a resuscitation management system 500, consistent with one or more exemplary embodiments of the present disclosure. In an exemplary embodiment, resuscitation management system 500 may be functionally similar to resuscitation management system 400. In an exemplary embodiment, resuscitation management system 400 and resuscitation management system 500 may be functionally and/or structurally similar to resuscitation management device 100.

In an exemplary embodiment, resuscitation management system 500 may include a processing unit 502 similar to processing unit 404. In an exemplary embodiment, processing unit 502 may include at least one memory 504 similar to memory 412, and at least one processor 505 similar to processor 410 that may be coupled with memory 504. In an exemplary embodiment, processing unit 502 may further include a timer 506, an output assembly driver 508, an analog to digital (A/D) converter 510, a peripheral control interface driver 512, and a communication module driver 514. In an exemplary embodiment, resuscitation management system 500 may further include a sensor assembly 516 that may be similar to sensor assembly 402 and may be coupled to processing unit 502 via A/D converter 510. In an exemplary embodiment, resuscitation management system 500 may further include an output assembly 518 that may be coupled to output assembly driver 508, a peripheral control interface 520 that may be coupled to peripheral control interface driver 512, a communication module 522 that may be coupled to communication module driver 514. In an exemplary embodiment, elements of resuscitation management system 500 may be coupled with each other via a wired, wireless, or a combination of wired and wireless network, which is represented by connecting solid lines in FIG. 5. For simplicity, some routine elements such as power supplies, touch screen interfaces, buttons, switches, electronic jumpers, and wires and/or connectors are omitted. In an exemplary embodiment, various elements of processing unit 502 may be directly connected to other elements of resuscitation management system 500 or may be indirectly connected to other elements via an internal network of wired, wireless, or a combination of wired and wireless network, illustrated by solid interconnecting lines in FIG. 5. In an exemplary embodiment, various elements of processing unit 502 may be indirectly connected to other elements of resuscitation management system 500 via communication module driver 514 or an external network (not illustrated).

In an exemplary embodiment, memory 504 may be a computer-readable media or a volatile memory unit or a non-volatile memory unit. In an exemplary embodiment, memory 504 may be a hard disk, a floppy disk, a tape device, a flash memory data storage device, a thumb drive, a solid-state memory (SSD), a read-only memory (ROM), or an optical disk device, or any other similar memory devices or storage devices.

In an exemplary embodiment, memory 504 may be configured to store software, codes, or other forms of executable instructions that may be retrieved by processor 505 or other components of processing unit 502 to enable them to perform various functions. In an exemplary embodiment, each of the various components of processing unit 502, such as processor 505 may include internal storages to store their software instructions or codes to enable them to perform various functions without requiring memory 504.

In an exemplary embodiment, memory 504 may further contain reference tables including the limits of target values that may be used to compare or interpret the measurements received from sensor assembly 516. For example, memory 504 may include a target number of breaths per certain time intervals according to the determined type of patient, target range of certain breathing parameters, such as I:E ratio, tidal volume, or minute ventilation according to the determined type of a patient and medical condition of a patient. As used herein, determining a type for a patient may refer to determining if a patient is adult, child or infant and if a patient is a human or animal.

In an exemplary embodiment, memory 504 may further contain information and/or executable instruction to control the operation of the various components of processing unit 502, for example running various components of resuscitation management system 500, testing various components of resuscitation management system 500, such as testing the battery capacity, or calibrating various components of resuscitation management system 500.

In an exemplary embodiment, processing unit 502 may store all or part of the measured values throughout a resuscitation event performed by a manual resuscitation bag similar to manual resuscitator 102. In an exemplary embodiment, the stored values may include one or a combination of multiple parameters, such as the age of the patient (infant, child, adult), the type of the patient (human, animal), the time and date of the resuscitation event, the total number of breaths delivered to the patient, the total number of proper breaths delivered to the patient, the total number of improper breaths delivered to the patient, breathing rate at each time point; average breathing rate per certain time interval, retrieved values from a reference table that may be stored in memory 504, squeezing or compressing speed of bag 104 of manual resuscitator 102, duration of inspirations, duration of expirations, time interval between any inspiration and expiration, or any other similar measured parameters by sensor assembly 516 or calculated parameters by processor 505.

In an exemplary embodiment, processing unit 502 may transfer the stored parameters on memory 504 to an external system, such as a computer, a tablet, or a mobile phone via communication module driver 514, or directly via communication module 522. Such stored history of measured and calculated data may be used for further evaluation of the quality of a given resuscitation event, or performance of a user during a resuscitation event. In certain cases, where a resuscitated patient may not survive, the history may provide evidence of an acceptable performance of artificial breathing, which may later be used to rule out hyperventilation or hypoventilation as a cause of death.

In an exemplary embodiment, peripheral control interface driver 512 may be connected to peripheral control interface 520 of resuscitation management system 500. In an exemplary embodiment, peripheral control interface 520 may be configured similar to I/O interface 414 of resuscitation management system 400 and may include touchscreens, buttons, switches, keypads, or potentiometers to let a user, such as a caregiver interact with processing unit 502 to initiate, continue or stop desired functions, or to input, alter, or delete at least one of the target values, the calculated values, and the calculated derivative values. In an exemplary embodiment, peripheral control interface 520 may be used to turn on or off resuscitation management system 500.

Figure 6:
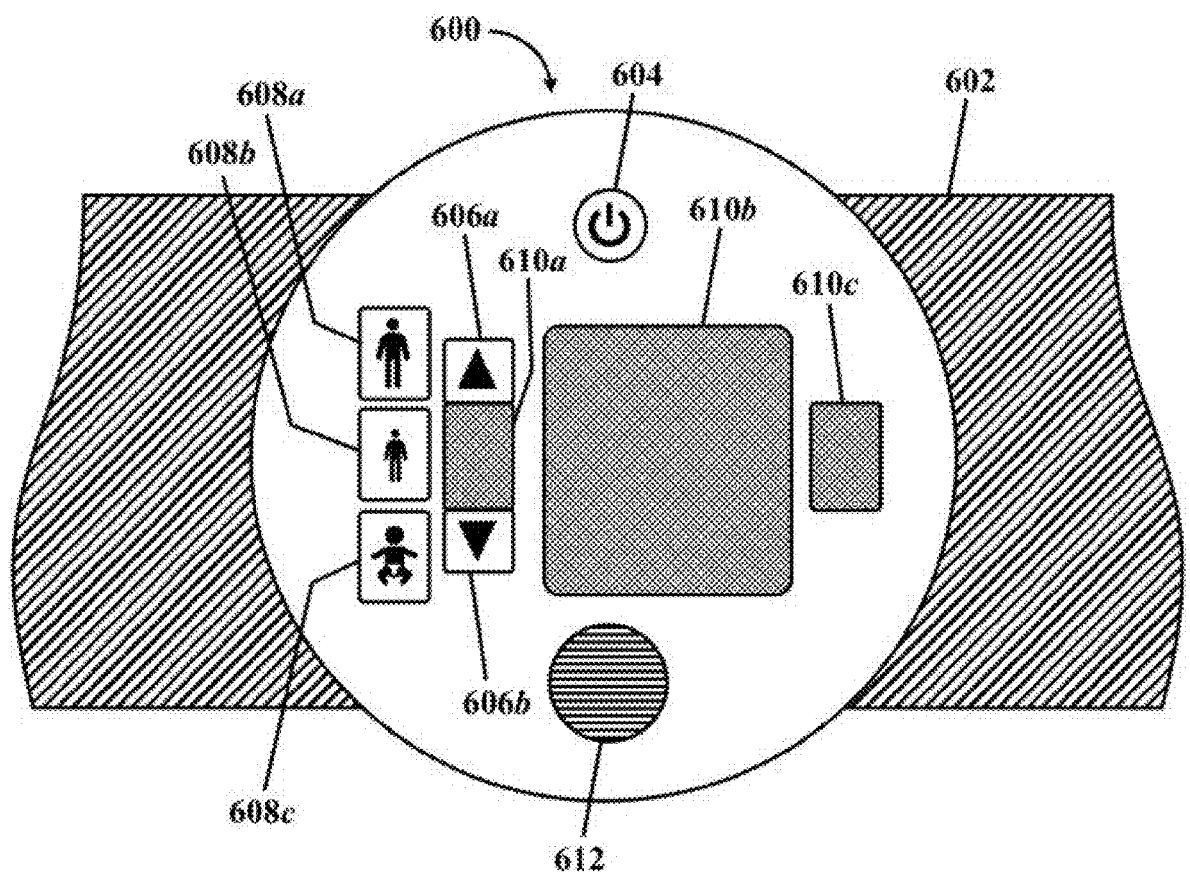
FIG. 6 illustrates a resuscitation management device, consistent with one or more exemplary embodiments of the present disclosure.

FIG. 6 illustrates a resuscitation management device 600, consistent with one or more exemplary embodiments of the present disclosure. In an exemplary embodiment, resuscitation management device 600 may be similar to resuscitation management device 100. In an exemplary embodiment, resuscitation management device 600 may include a sensing element similar to sensing element 120 and a sensible element similar to sensible element 118, which are both obscured from view in FIG. 6.

In an exemplary embodiment, resuscitation management device 600 may be attached to a manual resuscitator, such as manual resuscitator 102 by utilizing a flexible band, such as flexible band 602. In an exemplary embodiment, I/O interface 414 of resuscitation management system 400 may be configured as peripheral control interface 520 and output assembly 518 of system 500. In an exemplary embodiment, resuscitation management device 600 may include a peripheral control interface similar to peripheral control interface 520, which is referred to herein after with the same reference numeral. In an exemplary embodiment, peripheral control interface 520 may include an On/Off switch 604 that may be utilized for turning resuscitation management device 600 on or off In an exemplary embodiment, peripheral control interface 520 may further include adjustment buttons (606a and 606b) that may be utilized for adjusting various parameters, such as a desired breathing rate, a brand name of an exemplary manual resuscitator being used, and a type of compression (one-handed or two-handed). In an exemplary embodiment, peripheral control interface 520 may further include optional buttons (608a, 608b, and 608c) that may be utilized by a user to select an age group for a patient. For example, button 608a may be dedicated to selecting an adult age group, button 608b may be dedicated to selecting a child age group, and button 608c may be dedicated to selecting an infant age group.

In an exemplary embodiment, memory 412 may further store a database of commercially available manual resuscitators and their associated parameters, such as their respective volumes. In an exemplary embodiment, adjustment buttons (606a and 606b) may further be utilized to select a specific manual resuscitator from the stored database of commercially available manual resuscitators. In an exemplary embodiment, memory 412 may further store volumetric data for one-handed and two-handed compression of each respective commercially available manual resuscitators. Each commercially available manual resuscitator may have a specific internal volume and compressing an exemplary bag of a manual resuscitator by one hand or two hands may push out different volumes of breathing gases out of an exemplary bag. In an exemplary embodiment, such volumetric data for commercially available manual resuscitators and volumetric data for one-handed and two-handed compression of each respective commercially available manual resuscitator may allow for calculating various volumes of breathing gases delivered to a patient in various scenarios created due to utilizing different manual resuscitators and different types of compression (one-handed or two handed).

In an exemplary embodiment, memory 412 may further store executable instructions to urge processor 410 to calculate an extent of compression of bag 104 based at least in part on the amount of change in a distance between sensing element 120 and sensible element 118 during compression of bag 104. In other words, for a given change in a distance between sensing element 120 and sensible element 118, processor 410 may be configured to calculate how much an internal volume of bag 104 may change, based at least in part on volumetric data stored in memory 412 for each commercially available manual resuscitator.

In an exemplary embodiment, memory 412 may further store a 'bag compression-breathing volume' curve that may provide information regarding a volume of a delivered ventilation based at least in part on an extent of compression of bag 104. As used herein, a bag compression-breathing volume curve may be obtained for each available manual resuscitator by calibration measurements. An exemplary bag compression-breathing volume may correlate an extent of compression of a bag to a volume of breathing gases pushed out of the bag for that extent of compression. For example, an exemplary compression-breathing volume may show how much breathing gas will be pushed out of a specific commercially available bag for a 50% compression of that specific commercially available bag. In an exemplary embodiment, memory 412 may further store two 'bag compression-breathing volume' curves for each commercially available manual resuscitator, one curve for a one-handed compression of a bag of the manual resuscitator and one curve for a two-handed compression of the bag of the manual resuscitator. For example, a bag compression-breathing volume curve for a one-handed compression of a commercially available adult Ambu Spur II manual resuscitator may show that a 50% one-handed compression of a bag of the adult Ambu Spur II manual resuscitator with a 1475 ml volume may deliver 500 ml of air into a patient's airways. In another example, a bag compression-breathing volume curve for a two-handed compression of a commercially available adult Ambu Spur II manual resuscitator may show that a 50% two-handed compression of a bag of the adult Ambu Spur II manual resuscitator with a 1475 ml volume may deliver 1100 ml of air into a patient's airways.

In an exemplary embodiment, memory 412 may further store executable instructions to urge processor 410 to calculate a tidal volume based at least in part on the stored 'bag compression-breathing volume' curves. In an exemplary embodiment, memory 412 may further store executable instructions to urge processor 410 to calculate a minute ventilation based at least in part on the calculated tidal volume and the calculated breathing rate.

In an exemplary embodiment, output assembly 518 may include one or a combination of multiple displays (610a, 610b, and 610c), at least one audio device 612, at least one tactile device, such as a vibrator (not illustrated), and at least one mechanical actuator. In an exemplary embodiment, multiple displays (610a, 610b, and 610c) may refer to two-dimensional monochrome displays, color displays, touch screens, liquid crystal displays, electronic paper, electrophoretic displays, electroluminescent displays, seven-segment displays, organic light-emitting diode (OLED or organic LED), or any other relevant visual device. In an exemplary embodiment, display 610a may display an optimal value for the breathing per minute based at least in part on the age group, patient type, or a desirable breathing rate selected by a user.

In an exemplary embodiment, memory 412 may store executable instructions to urge processor 410 to calculate time-intervals between compressions of bag 104 based at least in part on the target breathing parameters, such as the target breathing rate. For example, for a target breathing rate of 12 breaths per minute, processor 410 may calculate the time interval between each pair of consecutive compressions to be 5 seconds. In an exemplary embodiment, memory 412 may store executable instructions to urge processor 410 to readjust time-intervals between compressions of bag 104 based on the performance of a user. For example, for a target breathing rate of 12 breaths per minute, responsive to a user having delivered only 5 breaths in 30 seconds instead of 6 breathes, processor 410 may be configured to readjust the time interval between the remaining 7 breaths to achieve the target breathing rate of 12 breaths per minute. For example, the time interval between the remaining 7 breaths may be readjusted to 6 seconds for the next 150 seconds to achieve the target breathing rate of 12 breaths per minute. In an exemplary embodiment, memory 412 may further store executable instructions to urge output assembly 518 to provide alarms corresponding to readjusted time intervals to guide a user to achieve target breathing parameters.

Figure 7:
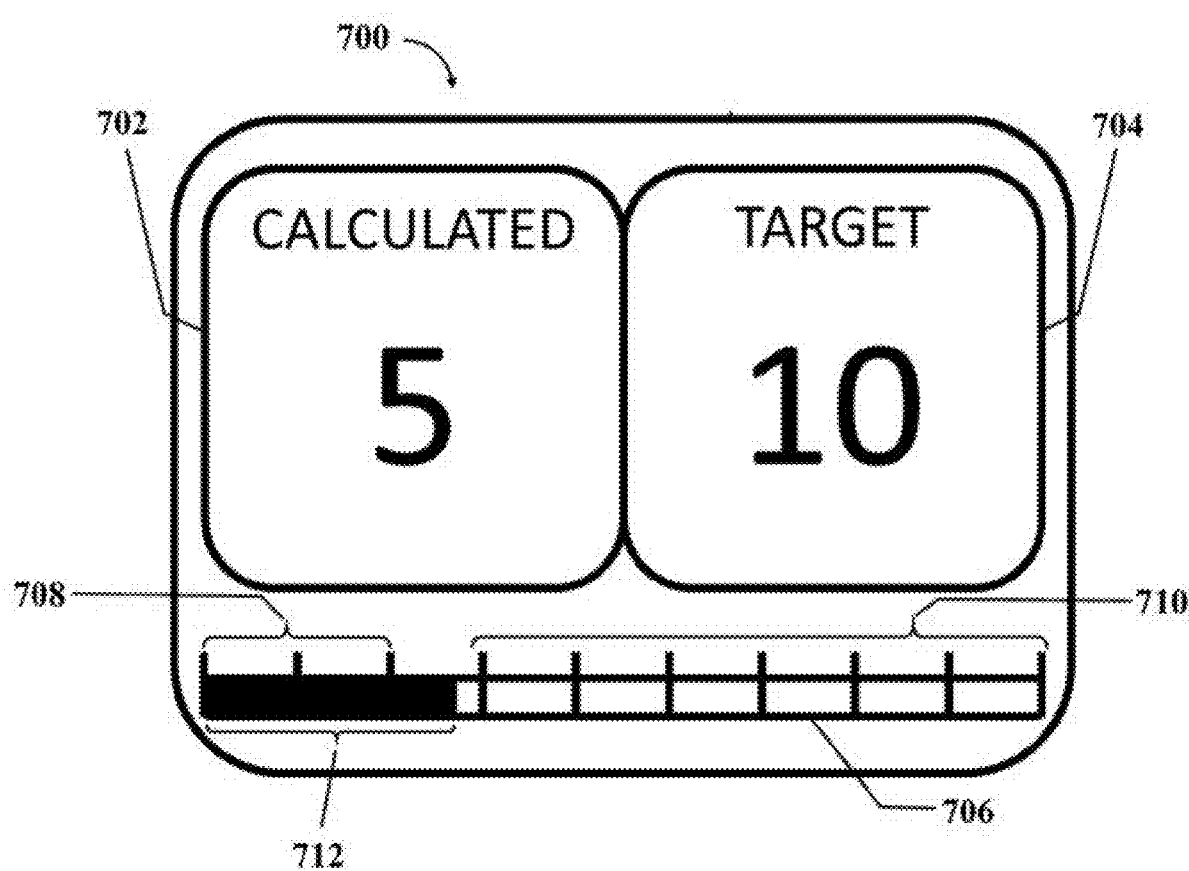
FIG. 7 illustrates a display of an output assembly, consistent with one or more exemplary embodiments of the present disclosure.

FIG. 7 illustrates a display 700 of output assembly 518, consistent with one or more exemplary embodiments of the present disclosure. In an exemplary embodiment, display 700 may be similar to display 510b. In an exemplary embodiment, display 700 may display various information regarding the operation and functions of a manual resuscitator coupled with a resuscitation management device similar to resuscitation management device 600 and various information regarding the resuscitation procedure. In an exemplary embodiment, display 700 may further display one or a combination of multiple values, such as a calculated breathing rate 702, a target breathing rate 704, alarm notifications (not illustrated), a timeline 706 illustrating timepoints 708 of given breaths and timepoints 710 of upcoming breaths based at least in part on one of the calculated breathing rate and calculated time intervals between consecutive compressions. In an exemplary embodiment, display 700 may further display a progress bar 712 illustrating time elapsed since the start of a certain breathing period. For example, timeline 706 may represent a 60 seconds breathing period, and progress bar 712 may illustrate that 14 seconds has passed since the start of a 60 seconds breathing period.

In an exemplary embodiment, display 700 may further display one or a combination of multiple values, such as an indication to show if the user is hypo-ventilating, normo-ventilating, or hyperventilating the patient, an indication to show the compression, or decompression of bag 104, an indication to show if the squeezing of bag 104 has been adequate to deliver a proper breathing; duration of compression or decompression of bag 104, compression/decompression speed, compression rate per minute or any arbitrary time interval, occurrence or non-occurrence of inspiration or expiration, calculated I:E ratio, target I:E ratio, elapsed time from the beginning of a resuscitation event, calculated tidal volume, target tidal volume, calculated minute ventilation, and target minute ventilation.

In an exemplary embodiment, display 700 may display a value, such as an exemplary value of current breathing rate per minute that is being delivered to a patient, and maybe an average of the number of the delivered breaths per certain time interval.

In an exemplary embodiment, output assembly 518 may further include one or more of monochrome light-emitting diodes (LEDs), multicolor LEDs, incandescent bulbs, surface mounted device (SMD) electroluminescent diode, or any other light-emitting elements. In an exemplary embodiment, audio device 612 may include a speaker, buzzer, piezo, or tone generator. In an exemplary embodiment, the tactile device may include one or a combination of pneumatic vibrators, electric vibrators, and hydraulic vibrators. In an exemplary embodiment, the vibrator may be an electric motor with an unbalanced mass on its driveshaft.

In an exemplary embodiment, output assembly 518 may provide alarms including one or a combination of multiple visual indications, such as light-emitting elements that are selectively turned on or turned off; audio indications that are generated by a speaker, buzzer, piezo, or tone generator; tactile indications that are generated by a vibrator; and mechanical indications that are generated by a mechanical actuator. In an exemplary embodiment, the alarm may be a lack of one or a combination of multiple visual indications, audio indications, tactile indications, or mechanical indications. For example, a visual, audio, or tactile signal may be generated continuously when there is no alarm, such as playing an audio signal of a certain frequency or a combination of various frequencies, when the user is using the bag-valve-mask in a target range of breathing parameters, such as delivering the target rate of breathing. In an exemplary embodiment, the alarm may be presented as a change in one or a combination of multiple visual indications, audio indications, or tactile indications. For example, a visual, audio, or tactile signal may change when there is an alarm, such as playing an audio signal of a different frequency, or a combination of various frequencies, when the user is not using the bag-valve-mask in a target range of breathing parameters (such as delivering a non-target rate of breathing).

Figure 8:
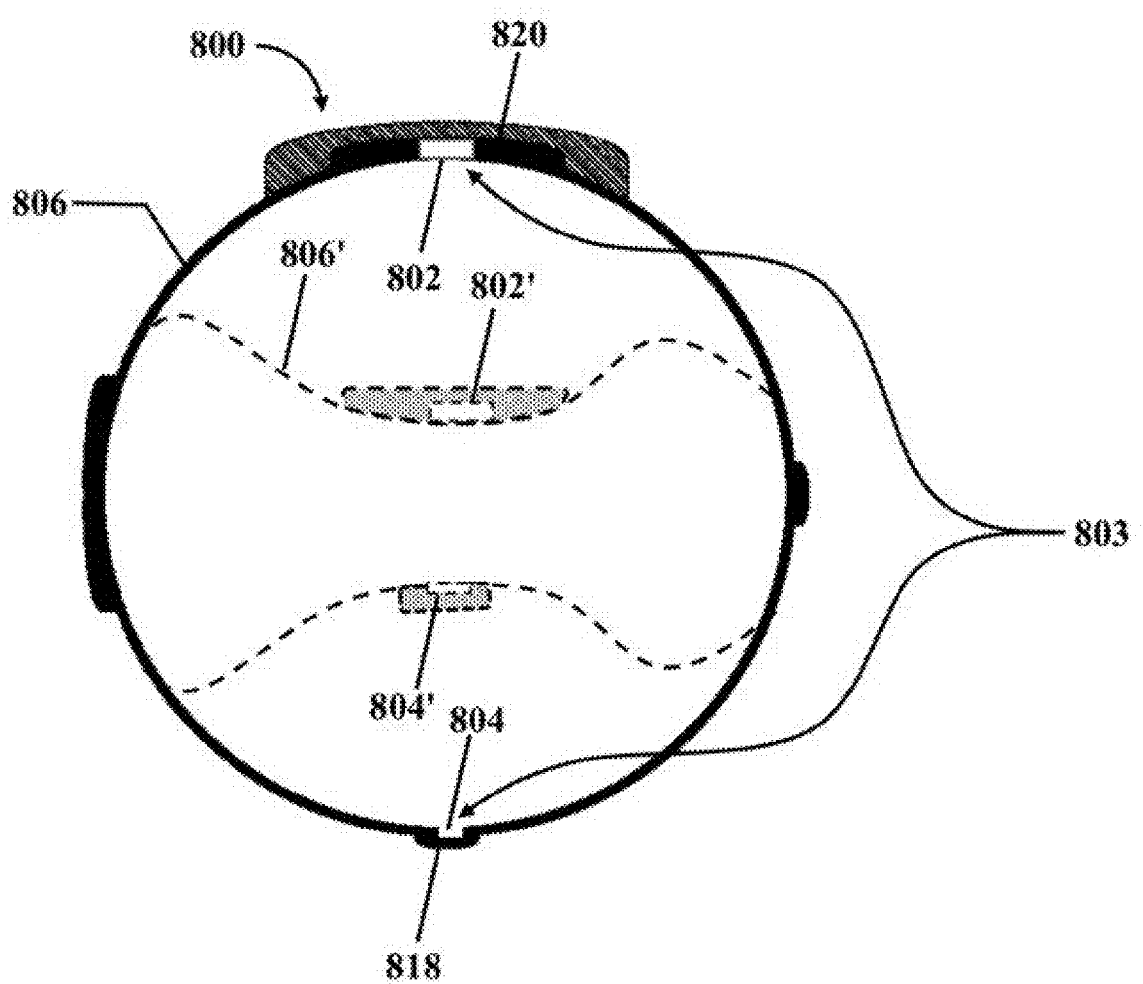
FIG. 8 illustrates a resuscitation management device, consistent with one or more exemplary embodiments of the present disclosure.

FIG. 8 illustrates a resuscitation management device 800, consistent with one or more exemplary embodiments of the present disclosure. In an exemplary embodiment, resuscitation management device 800 may be similar to resuscitation management device 100. In an exemplary embodiment, resuscitation management device 800 may include a sensor assembly 801 similar to sensor assembly 101 that may include a sensing element 820 similar to sensing element 120 and a sensible element 818 similar to sensible element 318. In an exemplary embodiment, resuscitation management device 800 may further include a mechanical actuator 803 that may be configured to generate mechanical indications. In an exemplary embodiment, mechanical actuator 803 may include an attracting element 802 and an attractable element 804. In an exemplary embodiment, attracting element 802 and attractable element 804 may include elements that may be arbitrarily magnetized to generate an electromagnetic field with a certain polarity and strength. For example, attracting element 802 and attractable element 804 may include a pair of electromagnets mounted on opposite sides of a resuscitation bag 806 along an axis perpendicular to a longitudinal axis of resuscitation bag 806. In an exemplary embodiment, such utilization of electromagnets as attracting element 802 and attractable element 804 may allow for selectively magnetizing attracting element 802 and attractable element 804 to either attract each other or repulse each other. Such attraction and repulsion of attracting element 802 and attractable element 804 may force resuscitation bag 806 to be compressed or decompressed on demand. For example, attracting element 802 and attractable element 804 may be magnetized such that opposite poles of attracting element 802 and attractable element 804 may face each other, which may lead to attracting element 802 and attractable element 804 attracting each other from a decompressed state to a compressed state designated by dash lines. Attracting element in the compressed state is referred to by reference numeral 802' and attractable element in the compressed state is referred to by reference numeral 804'. In an exemplary embodiment, mechanical actuator 803 may be a part of an output assembly similar to output assembly 518. In an exemplary embodiment, attracting element 802 and attractable element 804 may be coupled with a processing unit (not illustrated) similar to processing unit 502 either directly or via an output assembly driver (not illustrated) similar to output assembly driver 508.

In an exemplary embodiment, processing unit 502 may be configured to urge attracting element 802 and attractable element 804 to attract or repulse each other by sending command signals in the form of electric currents to attracting element 802 and attractable element 804. In an exemplary embodiment, processing unit 502 may be configured to manipulate polarities and strengths of magnetic fields generated by attracting element 802 and attractable element 804 by manipulating directions and amounts of the electric currents applied to attracting element 802 and attractable element 804. In an exemplary embodiment, attractable element 804 may further include a magnetic element, such as a permanent magnet or a ferromagnetic material.

As mentioned before, in an exemplary embodiment, output assembly 518 may provide alarms by generating mechanical indications. In an exemplary embodiment, such mechanical indications may be generated by mechanical actuator 803. For example, when a user is hyperventilating a patient, processing unit 502 may urge attracting element 802 or attractable element 804 to generate a magnetic field with a certain polarity and strength, such that attracting element 802 and attractable element 804 may attract each other to retain resuscitation bag 806 in a compressed state (designated by dash lines and referred to by 806'). In an exemplary embodiment, attracting element 802 and attractable element 804 attracting each other and thereby forcing resuscitation bag 806 to remain in a compressed state in response to a user hyperventilating a patient, may allow for locking resuscitation bag 806 and mechanically preventing the user to continue hyperventilation.

In an exemplary embodiment, peripheral control interface 520 may further be used to adjust other parameters and functions relevant to the operation of resuscitation management device 600, such as adjusting the target breathing rate, I:E ratio, or tidal volume, or minute ventilation, calibrating the sensor assembly, or muting output assembly 518. In an exemplary embodiment, the adjustments via peripheral control interface 520 may retrieve certain values from a reference table that may be stored in a memory of resuscitation management device 600, which may be configured similar to memory 504.

In an exemplary embodiment, processing unit 502 may further be configured to receive output signals of sensor assembly 516 and based at least in part on the received signals, initiate certain functions, such as turning on and off certain elements of resuscitation management system 500. For example, processing unit 502 may be configured to detect inactivity of the resuscitator, based at least in part on the received output signals of sensor assembly 516 and may initiate certain functions of resuscitation management system 500, such as presenting an alarm or turning off resuscitation management system 500, or even putting certain elements of resuscitation management system 500 to a low-power mode.

In an exemplary embodiment, utilizing such resuscitating management systems and devices similar to resuscitation management devices (100 and 600) or resuscitation management systems (400 and 500) may allow for determining if a manual resuscitator, such as manual resuscitator 102 is compressed or not, the duration of the compression, or the duration of lack of compression of bag 104; the speed of compression, or the speed of decompression of bag 104, number of compressions of bag 104, number of expansions of bag 104, rate of breathing per minute, rate of breathing during any arbitrary time intervals; or occurrence or non-occurrence of an inspiration or an expiration during a certain time interval.

In an exemplary embodiment, processing unit 502 may further be configured to store all or part of the measured values throughout a resuscitation event in memory 504. As used herein, the measured values throughout a resuscitation event may be one or a combination of multiple parameters, such as the age group of a patient, type of a patient, time and date of the resuscitation event, total number of breaths delivered to the patient, total number of proper breathing delivered to the patient, total number of improper breathing delivered to the patient, breathing rate at each time point, the average breathing rate per certain time interval, the speed of the squeezing of a resuscitating bag, such as bag 104, duration of any inspirations, duration of any expirations, time interval between any inspiration and expiration, and other similar parameters.

In an exemplary embodiment, processing unit 502 may further be configured to transfer the aforementioned stored parameters to an external system, such as a computer, a tablet, or a mobile phone via the communication module driver 514, or directly via communication module 522. In an exemplary embodiment, such stored parameters may be used for further evaluation of the quality of a resuscitation event, or the performance of a caregiver during a resuscitation event. For example, in case a patient dies during a resuscitation event, the stored parameters may provide evidence that may be utilized in an investigation for cause of death.

In an exemplary embodiment, processing unit 502 may further be configured to receive new executable instructions, for reconfiguring the built-in operating system (BIOS), or the firmware, or the software of the components of resuscitation management system 500. Such new executable instructions may temporarily or permanently be stored on memory 504. The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for description and not of limitation, such that the terminology or phraseology of the present specification is to be interpreted by the skilled artisan in light of the teachings and guidance.

The breadth and scope of the present disclosure should not be limited by any of the above-described exemplary embodiments but should be defined only in accordance with the following claims and their equivalents.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps. Moreover, the word "substantially" when used with an adjective or adverb is intended to enhance the scope of the particular characteristic, e.g., substantially planar is intended to mean planar, nearly planar and/or exhibiting characteristics associated with a planar element. Further use of relative terms such as "vertical", "horizontal", "up", "down", and "side-to-side" are used in a relative sense to the normal orientation of the apparatus.

What is claimed is:

1. A resuscitating management system for a manual resuscitator, the system comprising:
   a radio frequency identification (RFID) tag configured to be mounted on a first side of a bag of the manual resuscitator, the RFID tag configured to transmit information indicative of the presence of the RFID tag;
   an RFID reader configured to be mounted on an opposite second side of the bag, the RFID reader configured to generate an output signal corresponding to the presence of the RFID tag responsive to receiving the information transmitted by the RFID tag; and
   a flexible band, wherein the RFID reader is attached on the flexible band and the RFID tag is attached on the flexible band spaced from the RFID reader along a length of the flexible band, the flexible band configured to be wearable around the bag, the RFID tag positioned at the first side of an outer surface of the bag and the RFID reader positioned at the opposing second side of the outer surface of the bag responsive to the flexible band being worn around the bag,
   wherein the RFID reader is configured to receive the information transmitted by the RFID tag responsive to the RFID tag being at a distance from the RFID reader equal to or smaller than a predetermined threshold.

2. The system of claim 1, wherein the bag is squeezable along a first axis between a decompressed state and a compressed state, the RFID tag and the RFID reader aligned at opposite sides of the bag along the first axis, the RFID tag and the RFID reader at a first distance from each other in the decompressed state, the RFID tag and the RFID reader at a second distance from each other in the compressed state, the predetermined threshold set equal to the second distance.

3. The system of claim 2, wherein the information transmitted by the RFID tag comprises at least a radio frequency signal, the RFID reader further configured to measure a strength of the radio frequency signal transmitted by the RFID tag and to generate a signal strength data corresponding to the measured strength of the radio frequency signal.

4. The system of claim 3, further comprising:
   at least one processor coupled to the RFID reader; and
   at least one memory coupled to the at least one processor, the at least one memory storing executable instructions to urge the at least one processor to:
   receive a plurality of output signals from the RFID reader;
   associate each received output signal of the plurality of output signals with a delivered ventilation; and
   calculate a breathing rate by counting the delivered ventilations during a time interval.

5. The system of claim 4, wherein the at least one memory further stores executable instructions to urge the at least one processor to:
   receive a plurality of signal strength data from the RFID reader during the time interval;
   calculate a change in signal strength over the time interval based on the plurality of signal strength data;
   associate the change in signal strength over the time interval with a compression/decompression speed of the bag; and
   calculate an inspiratory to expiratory (I:E) ratio based at least in part on the compression/decompression speed of the bag.

6. The system according to claim 5, wherein the at least one memory further stores executable instructions to urge the at least one processor to:
   calculate a distance between the RFID reader and the RFID tag at a given instance by correlating the signal strength data received from the RFID reader at the given instance to the distance between the RFID reader and the RFID tag at the given instance;
   calculate a compression extent of the bag at the given instance by correlating the distance between the RFID reader and the RFID tag at the given instance to the compression extent of the bag; and
   calculate a tidal volume for each delivered ventilation by correlating the compression extent of the bag to a volume of breathing gases pushed out of the bag.

7. The system according to claim 6, wherein the at least one memory further stores executable instructions to urge the at least one processor to calculate a minute ventilation by calculating a sum of the calculated tidal volumes for the delivered ventilations in one minute.

8. The system of claim 7, further comprising an input/output (I/O) interface, the at least one processor further coupled to the I/O interface, wherein the at least one memory further stores executable instructions to urge the at least one processor to provide information on the I/O interface based at least in part on a plurality of calculated breathing parameters, the plurality of calculated parameters comprising the calculated breathing rate, the calculated I:E ratio, the calculated tidal volume, and the calculated minute ventilation.

9. The system of claim 8, wherein the I/O interface comprises at least one of a visual device, an audio device, a tactile device, and a mechanical device, the information provided by the at least one of the visual device, the audio device, the tactile device, and the mechanical device comprises one or more indications representing the plurality of calculated breathing parameters.

10. The system of claim 9, wherein the I/O interface is configured to produce a plurality of indications, the plurality of indications comprising at least one of a visual indication, an audio indication, a tactile indication, and a mechanical indication.

11. The system of claim 10, wherein the mechanical device comprises:
    an attracting element comprising an electromagnet, the attracting element configured to be mounted on the first side of the bag of the manual resuscitator;

an attractable element comprising at least one of a permanent magnet, a ferromagnetic material, and an electromagnet, the attractable element configured to be mounted on the opposite second side of the bag of the manual resuscitator, wherein the at least one memory stores executable instructions to urge the at least one processor to urge the attracting element to attract/repulse the attractable element by applying electrical currents of specific directions and strengths on at least one of the attracting element and the attractable element.

12. The system of claim 11, wherein the at least one memory stores executable instructions to urge the at least one processor to:
determine occurrence of hyperventilation based on the plurality of calculated breathing parameters; and
urge the mechanical device to lock the bag by urging the attracting element and the attractable element to attract each other responsive to the occurrence of hyperventilation.

13. The system of claim 1, further comprising:
a first radiofrequency shield enclosing the RFID reader, the first radiofrequency shield comprising a first cage made of a conductive material with a first opening, the first opening positioned at a side of the RFID reader facing the RFID tag; and
a second radiofrequency shield enclosing the RFID tag, the second radiofrequency shield comprising a first cage made of the conductive material with a second opening, the second opening positioned at a side of the RFID tag facing the RFID reader,
wherein the conductive material comprises at least one of galvanized steel and copper.

14. The system of claim 3, wherein:
the information transmitted by the RFID tag comprises a first code transmitted via the radio frequency signal, and
the system further comprises:
at least one processor coupled to the RFID reader; and
at least one memory coupled to the at least one processor, the at least one memory storing executable instructions to urge the at least one processor to:
receive a plurality of output signals from the RFID reader;
associate each received output signal of the plurality of output signals with a delivered ventilation responsive to each received output signal comprising the first code; and
calculate a breathing rate by counting the delivered ventilations during a time interval.

15. The system of claim 10, the at least one memory further storing executable instructions to urge the at least one processor to urge the I/O interface to produce a first indication of the plurality of indications to guide a user to deliver a breathing at a certain instance.

16. The system of claim 10, wherein the at least one memory further stores a plurality of target breathing parameter ranges, the plurality of target breathing parameter ranges comprising a target breathing rate range, a target I:E ratio range, a target tidal volume range, a target minute ventilation range, the at least one memory further storing executable instructions to urge the at least one processor to:
compare a calculated breathing parameter of the plurality of calculated breathing parameters with a corresponding target breathing parameter range of the plurality of target breathing parameter ranges;

urge the I/O interface to produce a first indication of the plurality of indications responsive to the calculated breathing parameter being in the corresponding target breathing parameter range; and
urge the I/O interface to produce a second indication of the plurality of indications responsive to the calculated breathing rate being outside the target breathing parameter range.

17. The system of claim 16, wherein:
the plurality of target breathing parameter ranges further include subsets of the target breathing parameter ranges, each subset of the subsets of the target breathing parameter ranges associated with at least one of an age group, a medical condition of a patient, and a patient type,
the I/O interface is further configured to receive data from a user, the data comprising at least one of an age group, a medical condition of a patient, and a patient type,
the at least one memory further stores executable instructions to urge the at least one processor to:
select a subset of the subsets of the target breathing parameters based on at least one of the received age group, the received medical condition of a patient, and the received patient type;
compare each calculated breathing parameter of the plurality of the calculated breathing parameters with a corresponding target breathing parameter range of the selected subset of the subsets of the target breathing parameter ranges;
urge the I/O interface to produce a first indication of the plurality of indications responsive to each calculated breathing parameter of the plurality of calculated breathing parameters being in a respective target breathing parameter range of the selected subset of the subsets of the target breathing parameter ranges; and
urge the I/O interface to produce a second indication of the plurality of indications responsive to each calculated breathing parameter of the plurality of the calculated breathing parameters being outside the respective target breathing parameter range of the selected subset of the subsets of the target breathing parameter ranges.

18. A resuscitating management system for a manual resuscitator, the system comprising:
a radio frequency identification (RFID) tag configured to be mounted on a first side of a bag of the manual resuscitator, the RFID tag configured to transmit information indicative of the presence of the RFID tag;
an RFID reader configured to be mounted on an opposite second side of the bag, the RFID reader configured to generate an output signal corresponding to the presence of the RFID tag responsive to receiving the information transmitted by the RFID tag;
a first radiofrequency shield enclosing the RFID reader, the first radiofrequency shield comprising a first cage made of a conductive material with a first opening, the first opening positioned at a side of the RFID reader facing the RFID tag; and
a second radiofrequency shield enclosing the RFID tag, the second radiofrequency shield comprising a first cage made of the conductive material with a second opening, the second opening positioned at a side of the RFID tag facing the RFID reader,
wherein the RFID reader is configured to receive the information transmitted by the RFID tag responsive to the RFID tag being at a distance from the RFID reader equal to or smaller than a predetermined threshold.

19. The system of claim 18, wherein the conductive material comprises at least one of galvanized steel and copper.

* * * * *